(12) United States Patent
Son et al.

(10) Patent No.: US 11,975,039 B2
(45) Date of Patent: May 7, 2024

(54) HERBAL COMPOSITION FOR TREATMENT OF ATTENTION DEFICIT HYPERACTIVITY DISORDER

(71) Applicant: HELIXMITH CO., LTD., Seoul (KR)

(72) Inventors: Miwon Son, Gyeonggi-do (KR); Doo Suk Lee, Gyeonggi-do (KR); Sunyoung Kim, Seoul (KR); In-Jeong Nam, Seoul (KR)

(73) Assignee: HELIXMITH CO., LTD., Seoul (KR)

( * ) Notice: Subject to any disclaimer, the term of this patent is extended or adjusted under 35 U.S.C. 154(b) by 849 days.

(21) Appl. No.: 17/054,280

(22) PCT Filed: May 9, 2019

(86) PCT No.: PCT/KR2019/005558
§ 371 (c)(1),
(2) Date: Jun. 21, 2021

(87) PCT Pub. No.: WO2019/216664
PCT Pub. Date: Nov. 14, 2019

(65) Prior Publication Data
US 2021/0315958 A1 Oct. 14, 2021

(30) Foreign Application Priority Data
May 10, 2018 (KR) .................... 10-2018-0053954

(51) Int. Cl.
*A61K 36/53* (2006.01)
*A23L 33/105* (2016.01)
(Continued)

(52) U.S. Cl.
CPC ............ *A61K 36/53* (2013.01); *A23L 33/105* (2016.08); *A61K 31/445* (2013.01); *A61K 36/77* (2013.01);
(Continued)

(58) Field of Classification Search
None
See application file for complete search history.

(56) References Cited

U.S. PATENT DOCUMENTS

| 2014/0243291 A1 | 8/2014 | Guenther et al. |
| 2015/0266911 A1 | 9/2015 | Guenther et al. |

(Continued)

FOREIGN PATENT DOCUMENTS

| CN | 101658663 A | 3/2010 |
| CN | 103933452 A | 7/2014 |

(Continued)

OTHER PUBLICATIONS

English language translation of CN 104208559 A. (Year: 2014).*

(Continued)

*Primary Examiner* — Dominic Lazaro
(74) *Attorney, Agent, or Firm* — Harness, Dickey & Pierce, P.L.C.

(57) ABSTRACT

Disclosed are a pharmaceutical composition for treatment of attention deficit hyperactivity disorder and a food composition for alleviation of attention deficit hyperactivity disorder, each of which contains as an active ingredient a mixture extract of Longan Arillus, Salviae Miltiorrhizae Radix, Gastrodiae Rhizoma, and Liriopis seu Ophiopogonis Tuber, wherein the compositions containing as an active ingredient a mixture extract of Longan Arillus, Salviae Miltiorrhizae Radix, Gastrodiae Rhizoma, and Liriopis seu Ophiopogonis Tuber of the present disclosure inhibits the hyperactivity of glutamate receptors, which is known to be a cause of attention deficit hyperactivity disorder, alleviates clinical symptoms (attention decrease and hyperactivity) of child patients, and shows an improvement effect in fMRI examination results, and thus can be advantageously used as a medicine for attention deficit hyperactivity disorder or a (Continued)

food for alleviation of attention deficit hyperactivity disorder.

9 Claims, 6 Drawing Sheets

(51) Int. Cl.
  *A61K 31/445*    (2006.01)
  *A61K 36/77*    (2006.01)
  *A61K 36/8965*    (2006.01)
  *A61K 36/8988*    (2006.01)
  *A61P 25/00*    (2006.01)

(52) U.S. Cl.
  CPC ...... *A61K 36/8965* (2013.01); *A61K 36/8988* (2013.01); *A61P 25/00* (2018.01); *A61K 2236/331* (2013.01); *A61K 2236/333* (2013.01)

(56) References Cited

U.S. PATENT DOCUMENTS

| | | |
|---|---|---|
| 2017/0049765 A1 | 2/2017 | Guenther et al. |
| 2019/0142815 A1 | 5/2019 | Guenther et al. |

FOREIGN PATENT DOCUMENTS

| | | | | |
|---|---|---|---|---|
| CN | 104208559 | A | * 12/2014 | |
| CN | 106110150 | A | * 11/2016 | ............ A61K 35/02 |
| KR | 10-2003-0027945 | A | 4/2003 | |
| KR | 10-2007-0040209 | A | 4/2007 | |
| KR | 10-0725839 | B1 | 12/2007 | |
| KR | 10-2011-0140015 | A | 12/2011 | |
| KR | 2013-0130069 | A | 11/2013 | |
| KR | 10-2014-0081761 | A | 7/2014 | |

OTHER PUBLICATIONS

English language translation of CN 106110150 A. (Year: 2016).*
Notice of Allowance from corresponding Korean Patent Application No. 10-2019-0054547, dated Dec. 22, 2021.
Cubo, E., et al,; Donepezil Use in Children and Adolescents with Tics and Attention-Deficit/Hyperactivity Disorder: An 18-Week, Single-Center, Dose-Escalating, Prospective, Open-Label Study, Clinical Therapeutics/vol. 30, No. 1, 2008, pp. 182-189.
Wilens, T. E., et al.; "Adjunctive Donepezil in Attention Deficit Hyperactivity Disorder Youth: Case Series", Journal of Child and Adolescent Psychopharmacology, vol. 10, No. 3, 2000, pp. 217-222.
International Search Report, dated Aug. 26, 2019, in corresponding International Patent Application No. PCT/KR2019/005558, with English translation.
Kim, et al. (2004) "3 Case Reports of ADHD Children treated with Acupuncture and Herbal Medicine.", *Journal of Oriental Neuropsychiatry*, 15(1):239-246.
Kwon, PhD, et al. (2015) "Effects of the Combination Herbal Extract on Working Memory and White Matter Integrity in Healthy Individuals with Subjective Memory Complaints: A Randomized, Double-Blind, Placebo-Controlled Clinical Trial.", *Korean J Biol Psychiatry*, 22(2):63-77.
Lee, et al. (2014) Ameliorating Effects of HX106N, a Water-Soluble Botanical Formulation, on $A\beta_{25-35}$-Induced Memory Impairment and Oxidative Stress in Mice., *Biol. Pharm. Bull.*, 37(6) 954-960.
Lee, et al. (2014) "Effects of HX106N, a Water-Soluble Botanical Formulation on Scopolamine-Induced Memory Impairment in Mice.", *Korean J. Food & Nutr.*, 27(4):673-677. (http://dx.doi.org/10.9799/ksfan.2014.27.4.673).
Lee, et al. (2015) "Effective suppression of nitric oxide production by HX106N through transcriptional control of heme oxygenase-1.", *Experimental Biology and Medicine.*, 240:1136-1146. DOI: 10.1177/1535370214567612.
Office Action from corresponding Korean Patent Application No. 10-2019-0054547, dated Mar. 4, 2021.

* cited by examiner

HERBAL COMPOSITION FOR TREATMENT OF ATTENTION DEFICIT HYPERACTIVITY DISORDER

CROSS-REFERENCE TO RELATED APPLICATIONS

This application is a national phase application of PCT Application No. PCT/KR2019/005558, filed on May 9, 2019, which claims the benefit of and priority to Korean Patent Application No. 10-2018-0053954, filed May 10, 2018. The entire disclosures of the applications identified in this paragraph are incorporated herein by references.

FIELD

This application claims priority to and the benefit of Korean Patent Application No. 10-2018-0053954 filed in the Korean Intellectual Property Office on 10 May 2018, the disclosure of which is incorporated herein by reference.

The present disclosure relates to a herbal medicine composition for treatment of attention deficit hyperactivity disorder.

BACKGROUND

Attention deficit hyperactivity disorder (ADHD) is one of the most common psychiatric conditions in childhood and adolescence and is a chronic disease that make it difficult for one to regulate one's own behavior. Typical symptoms of attention deficit hyperactivity disorder are sustained distraction, hyperactivity, and impulsivity, and most patients have these three symptoms in combination. In general, attention deficit hyperactivity disorder consistently shows related symptoms, unlike a decrease in attention that temporarily occurs due to a decrease in physical strength, fatigue, or the like. Attention deficit hyperactivity disorder is one of neurodevelopmental disorders, and the main causes thereof are the dysfunction of receptors of dopamine, norepinephrine, and glutamate, which are neurotransmitters that regulate attention in the brain. In addition to these, anatomical factors, genetic factors, and environmental factors are also included in the causes thereof.

One of the currently most commonly used medicines for attention deficit hyperactivity disorder is mainly a central nervous system (CNS) stimulant, and a typical example thereof is methylphenidate, which is known to regulate neurotransmitters, such as dopamine and norepinephrine. However, these psychoactive drugs are known to have a risk of dependence and abuse and to cause side effects, such as irritability, insomnia, loss of appetite, headache, and dizziness. An example of a non-stimulant medicine is atomoxetine, which has a risk of side effects in children with heart diseases and has non-excellent drug efficacy compared with stimulants. Therefore, medicines that have a low risk of side effects and excellent effects need to be urgently developed.

Since abnormal glutamate signaling in patients with attention deficit hyperactivity disorder was confirmed, the development of medicines capable of regulating AMPA (α-amino-3-hydroxy-5-methyl-4-isoxazolepropionic acid) receptor and NMDA (N-methyl-D-aspartate) receptor, which are glutamate receptors, is ongoing. Actually, it has been reported that the increased glutamate was reduced to the normal level by ADHD medicines in the prefrontal cortex and striatum of pediatric patients with attention deficit hyperactivity disorder, and attempts are being made to apply NMDA antagonists, such as the dementia drug memantine, to patients with attention deficit hyperactivity disorder (Caney et al., Biol Psychiatry. 15; 53(2):184-7, 2003, Robert L et al., J Child Adolesc Psychopharmacol. 17(1):19-33, 2007). It has also been known that attention deficit hyperactivity disorder is affected by whether AMPA receptor is active or not, considering that the activity of the AMPA receptor is increased in ADHD rat models.

The herbal medicine composition HX106 already developed by the present inventors is a herbal medicine composition composed of Longan Arillus, Salviae Miltiorrhizae Radix, Gastrodiae Rhizoma, and Liriopis seu Ophiopogonis Tuber, and has been known to have a memory improvement effect or an anti-dementia effect (KR10-1601860; Kwon et al., Korean J Biol Psychiatry 22(2):63-77, 2015). However, the effects of the herbal medicine composition on treatment of attention deficit hyperactivity disorder having various causes and symptoms as above have not yet been known.

Throughout the entire specification, many patent documents are referenced and their citations are represented. The disclosures of cited papers and patent documents are entirely incorporated by reference into the present specification, and the level of the technical field within which the present disclosure falls and details of the present disclosure are explained more clearly.

SUMMARY

The present inventors, while conducting a variety of research using herbal medicine compositions containing Longan Arillus, Salviae Miltiorrhizae Radix, Gastrodiae Rhizoma, and Liriopis seu Ophiopogonis Tuber extracts, discovered that these compositions have not only existing known memory improvement and anti-dementia effects but also effects on attention deficit hyperactivity disorder, and thus completed the present disclosure.

Accordingly, an aspect of the present disclosure is to provide a pharmaceutical composition for treatment of attention deficit hyperactive disorder.

Another aspect of the present disclosure is to provide a food composition for alleviation of attention deficit hyperactive disorder.

Still another aspect of the present disclosure is to provide a method for treatment of attention deficit hyperactive disorder.

Other purposes and advantages of the present disclosure will become more obvious when taken with the following detailed description of the invention, claims, and drawings.

In accordance with an aspect of the present disclosure, there is provided a pharmaceutical composition for treatment of attention deficit hyperactivity disorder (ADHD), the pharmaceutical composition containing: (a) as an active ingredient, a mixture extract of Longan Arillus, Salviae Miltiorrhizae Radix, Gastrodiae Rhizoma, and Liriopis seu Ophiopogonis Tuber; and (b) a pharmaceutically acceptable carrier.

Longan Arillus, Salviae Miltiorrhizae Radix, Gastrodiae Rhizoma, and Liriopis seu Ophiopogonis Tuber, which pertain to the active ingredient provided in the present disclosure, have characteristics and specific actions as below.

Longan Arillus is obtained by drying the aril of *Euphoria longan* (Lour.) STEUD., an evergreen tree in the family *Sapindaceae*. It has been known that Longan Arillus is rich in tartaric acid, vitamins B1, B2, and C, and the like and has an antioxidant action and an immune function activating action.

Salviae Miltiorrhizae Radix is obtained by drying the roots and rhizoma of a perennial plant belonging to the family *Labiatae*, preferably *Salvia miltiorrhiza* BGE., and is known to treat various pain diseases and abscesses (Kim Hocheol, Herbal Pharmacology, 332-333, 2004).

Gastrodiae Rhizoma is a perennial parasitic plant belonging to the family Orchidaceae and is a perennial herb that inhabits in Korea, China, Japan, and Taiwan. Gastrodiae Rhizoma as a herbal medicine substance herein is obtained by drying the tuber of *Gastrodia elata* BL., and treats various convulsive diseases and has been widely used for nervous system disorders, such as various types of headache, dizziness, and paralysis (Kim Changmin in et al. Grand Dictionary of Chinese Medicine, 4105-4110, 2004; and Kang Byungsoo et al. Herbology, 504-505, 2000).

Liriopis seu Ophiopogonis Tuber is the ampulla of the roots of *Liriope platyphylla* or *Ophiopogon japonicas*, which is a perennial herb belonging to the family *Liliaceae*. Liriopis seu Ophiopogonis Tuber has been known to have antipyretic, antiinflammatory, antitussive, expectorant, diuretic, cardiotonic, tonic, and antibacterial effects.

As used herein, the term "Longan Arillus extract" refers to an extract obtained from the arillus of *Euphoria longan* (Lour.) STEUD. The term "Salviae Miltiorrhizae Radix extract" refers to an extract obtained from various organs (e.g., root, rhizoma, fruit, stem, leaf, and flower) of *Salvia miltiorrhiza* BGE. Preferably, the Salviae Miltiorrhizae Radix extract refers to an extract obtained from the roots or rhizoma of *Salvia* miltiorrhiza BGE. The term "Gastrodiae Rhizoma extract" refers to an extract obtained from various organs (e.g., root, tuber, fruit, stem, leaf, and flower) of Gastrodiae Rhizoma. Preferably, the Gastrodiae Rhizoma extract refers to an extract obtained from the tuber of *Gastrodia* elate BL. The term "Liriopis seu Ophiopogonis Tuber extract" refers to an extract obtained from the ampulla of roots of *Liriope platyphylla*.

The Longan Arillus, Salviae Miltiorrhizae Radix, Gastrodiae Rhizoma, and Liriopis seu Ophiopogonis Tuber extracts used in the present disclosure may be purchased, or obtained by direct extraction from herbal medicines. The extraction may be performed after each herb medicine is cut or crushed into proper sizes.

When the extracts used in the composition of the present disclosure are obtained by direct extraction from the herb medicines Longan Arillus, Salviae Miltiorrhizae Radix, Gastrodiae Rhizoma, and Liriopis seu Ophiopogonis Tuber, various extraction solvents, such as polar solvents or non-polar solvents, may be used.

Appropriate examples of the polar solvents may include (i) water, (ii) C1 to C6 lower alcohols (specifically, methanol, ethanol, propanol, butanol, n-propanol, iso-propanol, n-butanol, 1-pentanol, 2-butoxyethanol, or ethylene glycol), (iii) acetic acid, (iv) dimethylformamide (DMFO), and (v) dimethyl sulfoxide (DMSO). Appropriate examples of the non-polar solvents include acetone, acetonitrile, ethyl acetate, methyl acetate, fluoroalkanes, pentane, hexane, 2,2,4-trimethyl pentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethyl amine, ethers, carbon tetrachloride, and tetrahydrofuran (THF).

The amounts of the extraction solvents may vary depending on the amounts of Longan Arillus, Salviae Miltiorrhizae Radix, Gastrodiae Rhizoma, and Liriopis seu Ophiopogonis Tuber, which are to be subjected to extraction, and specifically, the extraction solvents have a volume corresponding to 1-20 times, specifically, 5-15 times, more specifically, 5-12 times, or 7-12 times the weight of Longan Arillus, Salviae Miltiorrhizae Radix, Gastrodiae Rhizoma, Liriopis seu Ophiopogonis Tuber, or a mixture thereof. Most specifically, the extraction solvents have a volume corresponding to 10 times the weight of Longan Arillus, Salviae Miltiorrhizae Radix, Gastrodiae Rhizoma, Liriopis seu Ophiopogonis Tuber, or a mixture thereof.

The extraction temperature for the extracts of the present disclosure is not particularly limited, and may be, for example, 0° C. to 120° C. and, specifically, 20° C. to 95° C., 30° C. to 95° C., 40° C. to 95° C., 50° C. to 95° C., 60° C. to 95° C., 70° C. to 95° C., 80° C. to 95° C., or 85° C. to 95° C.

The extraction time of the extracts of the present disclosure is not particularly limited, and may be for example 1 hour to 10 days, specifically, 1 to 72 hours, 1 to 48 hours, 1 to 36 hours, 1 to 24 hours, 1 to 12 hours, 1 to 10 hours, or 1 to 6 hours. The extraction time may be more specifically, 2 to 72 hours, 2 to 48 hours, 2 to 36 hours, 2 to 24 hours, 2 to 12 hours, 2 to 10 hours, 2 to 6 hours, 3 to 72 hours, 3 to 48 hours, 3 to 36 hours, 3 to 24 hours, 3 to 12 hours, 3 to 10 hours, 3 to 8 hours, or 3 to 6 hours, and most specifically, 3 hours.

The extracts of the present disclosure may be extracted by known natural substance extraction. Examples of the extraction may include cold extraction, hot-water extraction, ultrasonic extraction, reflux cooling extraction, and heating extraction, and specifically, hot-water extraction. The extraction may be repeated one to ten times, and more specifically two to seven times.

According to an embodiment of the present disclosure, the Longan Arillus, Salviae Miltiorrhizae Radix, Gastrodiae Rhizoma, and Liriopis seu Ophiopogonis Tuber extracts used in the present disclosure may be obtained by extraction with an organic solvent, water, or a mixed solvent thereof. Examples of the organic solvent include C1 to C6 lower alcohols, petroleum ether, hexane, benzene, chloroform, methylene chloride, ethers, ethyl acetate, and acetone.

The concentration of the organic solvents, such as C1 to C6 lower alcohols, petroleum ether, hexane, benzene, chloroform, methylene chloride, ethers, ethyl acetate, and acetone, may be 1-100% (v/v), specifically 10-100% (w/w), 20-100% (w/w), 30-100% (w/w), 40-100% (w/w), 50-100% (w/w), 60-100% (w/w), 70-100% (w/w), or 80-100% (w/w), and more specifically 10-90% (w/w), 10-80% (w/w), 10-70% (w/w), 10-60% (w/w), 10-50% (w/w), 10-40% (w/w), or 10-30% (w/w), still more specifically 20-80% (w/w), 20-70% (w/w), 20-60% (w/w), 20-50% (w/w), 20-40% (w/w), or 20-30% (w/w), and most specifically 25% (w/w), but is not limited thereto.

According to still another embodiment of the present disclosure, the Longan Arillus, Salviae Miltiorrhizae Radix, Gastrodiae Rhizoma, and Liriopis seu Ophiopogonis Tuber extracts of the present disclosure may be prepared by extraction with water, a C1 to C6 lower alcohol, or a mixed solvent thereof as described above, or may be prepared by, after extraction and concentration (under reduced pressure), further extraction or fractionation with an organic solvent selected from the group consisting of petroleum ether, hexane, benzene, chloroform, methylene chloride, ethers, ethyl acetate, and acetone as described above.

The mixture extract of the Longan Arillus, Salviae Miltiorrhizae Radix, Gastrodiae Rhizoma, and Liriopis seu Ophiopogonis Tuber extracts used in the present disclosure may be prepared by mixing individual Longan Arillus, Salviae Miltiorrhizae Radix, Gastrodiae Rhizoma, and Liriopis seu Ophiopogonis Tuber extracts, or may be prepared by treating a mixture of the herb medicines Longan Arillus, Salviae Miltiorrhizae Radix, Gastrodiae Rhizoma, and Liriopis seu Ophiopogonis Tuber with an extraction solvent.

In the present disclosure, the Longan Arillus, Salviae Miltiorrhizae Radix, Gastrodiae Rhizoma, and Liriopis seu Ophiopogonis Tuber extracts may be used in the form of a crude extract that is obtained by extraction with a solvent, and may be used through high-purity purification.

As used herein, the term "extract" has a meaning that is commonly used as a crude extract in the art as described above and, broadly, encompasses a fraction obtained by additionally fractionating the extract. That is, the Longan Arillus, Salviae Miltiorrhizae Radix, Gastrodiae Rhizoma, and Liriopis seu Ophiopogonis Tuber extracts encompass not only ones obtained by using the above-described extraction solvents but also ones obtained by additionally applying a purification procedure to the extracts. For example, fractions obtained by passing the extracts through an ultra-filtration membrane with a predetermined molecular weight cut-off value and fractions obtained through various purification methods that are additionally performed, such as various types of chromatography (fabricated for separation depending on size, charge, hydrophobicity, or hydrophilicity), may also be included in the Longan Arillus, Salviae Miltiorrhizae Radix, Gastrodiae Rhizoma, and Liriopis seu Ophiopogonis Tuber extracts of the present disclosure. The Longan Arillus, Salviae Miltiorrhizae Radix, Gastrodiae Rhizoma, and Liriopis seu Ophiopogonis Tuber extracts used in the present disclosure may be prepared in a powder form by additional procedures, such as distillation under reduced pressure and freeze-drying or spray drying.

In an embodiment of the present disclosure, the complex herbal extract of the present disclosure is prepared by a method including the steps of:

(a) washing and drying Longan Arillus, Salviae Miltiorrhizae Radix, Gastrodiae Rhizoma, and Liriopis seu Ophiopogonis Tuber;

(b) crushing Longan Arillus, Salviae Miltiorrhizae Radix, Gastrodiae Rhizoma, and Liriopis seu Ophiopogonis Tuber;

(c) mixing Longan Arillus, Salviae Miltiorrhizae Radix, Gastrodiae Rhizoma, and Liriopis seu Ophiopogonis Tuber;

(d) adding the mixture of Longan Arillus, Salviae Miltiorrhizae Radix, Gastrodiae Rhizoma, and Liriopis seu Ophiopogonis Tuber to an extraction solvent having a volume (ml) corresponding to 1-20 times the weight (g) of the mixture;

(e) conducting extraction with stirring at 20-95° C. for 1-48 hours;

(f) filtering the extract, followed by concentration; and (g) drying the concentrated extract.

The order of the respective steps may be changed or omitted according to the needs of those skilled in the art, and the resultant product in each step may be directly prepared by a practitioner, or may be purchased.

According to a specific embodiment of the present disclosure, the Longan Arillus, Salviae Miltiorrhizae Radix, Gastrodiae Rhizoma, and Liriopis seu Ophiopogonis Tuber are washed and dried, and then mixed at a predetermined weight ratio. The mixture was then added to an extraction solvent having a volume (ml) corresponding to 1-20 times the weight (g) of the mixture, followed by extraction with good stirring at 20-95° C. for 1-48 hours. Thereafter, the extract was filtered, concentrated at 50-65° C. under reduced pressure, and freeze-dried to give a complex herbal extract (mixture extract) in a powder form.

According to a specific embodiment of the present disclosure, each of Longan Arillus, Salviae Miltiorrhizae Radix, Gastrodiae Rhizoma, and Liriopis seu Ophiopogonis Tuber is added to an extraction solvent having a volume (ml) corresponding to 1-20 times the weight (g) thereof, and then subjected to extraction with good stirring at 20-95° C. for 1-48 hours. Then, each extract was filtered, concentrated at 50-65° C. under reduced pressure, and freeze-dried to give a herbal medicine extract in a powder form. Then, the respective herbal medicine extracts are mixed at a predetermined weight ratio to give a complex herbal extract (mixture extract) in a powder form.

According to a specific embodiment of the present disclosure, Longan Arillus, Salviae Miltiorrhizae Radix, Gastrodiae Rhizoma, and Liriopis seu Ophiopogonis Tuber are mixed at a weight ratio of 3:3:1:5, and then water is added thereto with 10 times the total weight, followed by extraction under reflux at 90±5° C. for 3 hours. The extract was filtered, and concentrated at 50-65° C. under reduced pressure, and then the concentrate was freeze-dried to give a complex herbal medicine extract of Longan Arillus, Salviae Miltiorrhizae Radix, Gastrodiae Rhizoma, and Liriopis seu Ophiopogonis Tuber.

The mixture extract of Longan Arillus, Salviae Miltiorrhizae Radix, Gastrodiae Rhizoma, and Liriopis seu Ophiopogonis Tuber used in the present disclosure may contain Longan Arillus, Salviae Miltiorrhizae Radix, Gastrodiae Rhizoma, and Liriopis seu Ophiopogonis Tuber herbal extracts at a weight ratio of 1-10:1-10:1-10:1-10, 1:1-10:1-10:1-10, 1-10:1:1-10:1-10, 1-10:1-10:1:1-10, 1-10:1-10:1-10:1, 1:1:1-10:1-10, 1:1-10:1:1-10, 1:1-10:1-10:1, 1-10:1:1:1-10, 1-10:1:1-10:1, 1-10:1-10:1:1, 1:1:1:1-10, 1:1:1-10:1, 1:1-10:1:1, or 1-10:1:1:1.

Alternatively, the mixture extract may contain Longan Arillus, Salviae Miltiorrhizae Radix, Gastrodiae Rhizoma, and Liriopis seu Ophiopogonis Tuber herbal extracts at a weight ratio of 1-5:1-5:1-5:1-5, 1:1-5:1-5:1-5, 1-5:1:1-5:1-5, 1-5:1-5:1:1-5, 1-5:1-5:1-5:1, 1:1:1-5:1-5, 1:1-5:1:1-5, 1:1-5:1-5:1, 1-5:1:1:1-5, 1-5:1:1-5:1, 1-5:1-5:1:1, 1:1:1:1-5, 1:1:1-5:1, 1:1-5:1:1, or 1-5:1:1:1, or may contain the same at a weight ratio of 1-3:1-3:1-3:1-3, 1:1-3:1-3:1-3, 1-3:1:1-3:1-3, 1-3:1-3:1:1-3, 1-3:1-3:1-3:1, 1:1:1-3:1-3, 1:1-3:1:1-3, 1:1-3:1-3:1, 1-3:1:1:1-3, 1-3:1:1-3:1, 1-3:1-3:1:1, 1:1:1:1-3, 1:1:1-3:1, 1:1-3:1:1, 1-3:1:1:1, 1-3:1-3:1-5, or 1-3:1-3:1:1-5, and more specifically, 3:3:1:5.

The mixing ratio of the herbal medicine components described herein is determined on the basis of the weight of solids with solvents removed therefrom (in a case of a mixture of herbal medicine extracts) or the weights of herbal medicines per se (in a case of an extract of mixed herbal medicines).

As used herein, the term "to" or "-" used between two numerical values refers to a section between the numerical values including numerical values described before and after the term.

The composition of the present disclosure may be prepared as a pharmaceutical composition.

According to a specific embodiment of the present disclosure, the composition of the present disclosure is a pharmaceutical composition containing: (a) as an active ingredient, a mixture extract of Longan Arillus, Salviae Miltiorrhizae Radix, Gastrodiae Rhizoma, and Liriopis seu Ophiopogonis Tuber; and (b) a pharmaceutically acceptable carrier.

As used herein, the term "pharmaceutically effective amount" refers to an amount sufficient to achieve the efficacy of the mixture extract of Longan Arillus, Salviae Miltiorrhizae Radix, Gastrodiae Rhizoma, and Liriopis seu Ophiopogonis Tuber to treat attention deficit hyperactivity disorder (ADHD). The present disclosure is directed to a composition containing extracts extracted from the natural plant substances Longan Arillus, Salviae Miltiorrhizae Radix, Gastrodiae Rhizoma, and Liriopis seu Ophiopogonis Tuber. Since the administration of an excess of the composition causes no side effects in the human body, a person skilled in the art could select and implement the upper limits of the amounts of the extracts contained in the composition of the present disclosure within an appropriate range.

As proved in an exemplary embodiment as below, the complex herbal medicine extract (mixture extract) of Longan Arillus, Salviae Miltiorrhizae Radix, Gastrodiae Rhizoma, and Liriopis seu Ophiopogonis Tuber of the present disclosure showed an effect of inhibiting hyperactivity of glutamate receptors (AMPA receptor and NMDA receptor), which is one of the causes of ADHD, by inhibiting the binding between the glutamate receptors and ligands.

As provided in another exemplary embodiment of the present disclosure, the complex herbal medicine extract (mixture extract) of Longan Arillus, Salviae Miltiorrhizae Radix, Gastrodiae Rhizoma, and Liriopis seu Ophiopogonis Tuber of the present disclosure, when administered to ADHD child patients, showed effects of reducing attention decrease and hyperactivity impulsivity of the child patients.

In addition, as a result of fMRI examination on ADHD child patients receiving the complex herbal medicine extract (mixture extract) of Longan Arillus, Salviae Miltiorrhizae Radix, Gastrodiae Rhizoma, and Liriopis seu Ophiopogonis Tuber of the present disclosure, the activation of the brain regions associated with the concentration of child patients was induced and an effect of increasing the functional connectivity of the brain was exhibited.

When the composition of the present disclosure is prepared as a pharmaceutical composition, the pharmaceutical composition of the present disclosure may contain a pharmaceutically acceptable carrier. The pharmaceutically acceptable carrier is usually used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, and the like. The pharmaceutical composition of the present disclosure may further contain, in addition to the above ingredients, a lubricant, a wetting agent, a sweetening agent, a flavoring agent, an emulsifier, a suspending agent, a preservative, and the like. Appropriate pharmaceutically acceptable carriers and preparations are described in detail in Remington's Pharmaceutical Sciences (19th ed., 1995).

The pharmaceutical composition of the present disclosure may be administered orally or parenterally, and examples of parenteral administration may include intravenous administration, subcutaneous administration, intradermal administration, intramuscular administration, intranasal administration, mucosal administration, intradural administration, intraperitoneal administration, intraocular administration, and the like. Specifically, the pharmaceutical composition of the present disclosure may be administered orally.

The appropriate dose of the pharmaceutical composition of the present disclosure varies depending on factors, such as preparation method, administration manner, patient's age, body weight, and sex, morbid condition, diet, administration time, administration route, excretion rate, and response sensitivity. An ordinarily skilled practitioner can easily determine and prescribe a dose that is effective for desired treatment or prevention. According to a specific embodiment of the present disclosure, a daily dose of the pharmaceutical composition of the present disclosure is 0.001-1000 mg/kg. The daily dose of the pharmaceutical composition of the present disclosure may be, for example, 0.1-1000 mg/kg, 0.1-900 mg/kg, 0.1-800 mg/kg, 0.1-700 mg/kg, 0.1-600 mg/kg, 0.1-500 mg/kg, 0.1-400 mg/kg, 0.1-300 mg/kg, 0.1-200 mg/kg, 0.1-100 mg/kg, 0.1-50 mg/kg, 0.1-30 mg/kg, 0.1-20 mg/kg, 0.1-10 mg/kg, 0.1-7 mg/kg, or 0.1-5 mg/kg; specifically 1-1000 mg/kg, 1-900 mg/kg, 1-800 mg/kg, 1-700 mg/kg, 1-600 mg/kg, 1-500 mg/kg, 1-400 mg/kg, 1-300 mg/kg, 1-200 mg/kg, 1-100 mg/kg, 1-50 mg/kg, 1-30 mg/kg, 1-20 mg/kg, 1-10 mg/kg, 1-7 mg/kg, or 1-5 mg/kg; and more specifically, 1, 2, 3, 4, 5, 6, 7, 8, 9, 10, 11, 12, 13, 14, 15, 16, 17, 18, 19, or 20 mg/kg. In another embodiment of the present disclosure, the daily dose of the pharmaceutical composition of the present disclosure may be, for example, 100-900 mg/kg, 100-800 mg/kg, 100-700 mg/kg, 100-600 mg/kg, 100-500 mg/kg, 100-400 mg/kg, 100-300 mg/kg, or 100-200 mg/kg; specifically 200-900 mg/kg, 200-800 mg/kg, 200-700 mg/kg, 200-600 mg/kg, 200-500 mg/kg, 200-400 mg/kg, or 200-300 mg/kg; more specifically 300-900 mg/kg, 300-800 mg/kg, 300-700 mg/kg, 300-600 mg/kg, 300-500 mg/kg, or 300-400 mg/kg, 400-900 mg/kg, 400-800 mg/kg, 400-700 mg/kg, 400-600 mg/kg, or 400-500 mg/kg; and more specifically 100 mg/kg, 200 mg/kg, 300 mg/kg, 400 mg/kg, 500 mg/kg, 600 mg/kg, 700 mg/kg, 800 mg/kg, 900 mg/kg, or 1000 mg/kg, but is not limited thereto.

The pharmaceutical composition of the present disclosure may be prepared into a unit dosage form or in the form of being contained in a multi-dose container by using a pharmaceutically acceptable carrier and/or excipient according to a method that can be easily performed by a person skilled in the art to which the present disclosure pertains. The formulation may be in the form of a solution in an oily or aqueous medium, a suspension, or an emulsion, or in the form of an extract, a powder, granules, a tablet, or a capsule, and may further contain a dispersant or a stabilizer.

The pharmaceutical composition of the present disclosure may be administered in combination with a known compound or pharmaceutical composition having a treatment effect for attention deficit hyperactivity disorder.

According to another aspect of the present disclosure, there is provided a food composition for alleviation of ADHD, the food composition containing as an active ingredient, a mixture extract of Longan Arillus, Salviae Miltiorrhizae Radix, Gastrodiae Rhizoma, and Liriopis seu Ophiopogonis Tuber. The food composition may be used as a health functional food or may be added to various types of foods.

The present disclosure also provides a health functional food containing the food composition. Examples of the health functional food may include drinks, meats, chocolates, foods, confectionery, pizzas, instant noodles, other noodles, gums, ice creams, alcohol drinks, vitamin complexes, and health supplement foods.

The content of the mixture extract of the present disclosure contained in the food composition may be regulated as appropriate according to the form of food, the desired use, or the like, and is not particularly limited thereto. For example, the content of the mixture extract may be 0.001-30 wt % or 0.01-20 wt % of the entire food weight, and as for a health drink composition, the mixture extract may be contained at 0.001-15 g, 0.02-10 g, or 0.3-1 g relative to 100 ml of the health drink composition, but is not limited thereto.

The composition containing the mixture extract of Longan Arillus, Salviae Miltiorrhizae Radix, Gastrodiae Rhizoma, and Liriopis seu Ophiopogonis Tuber, when prepared as a food composition, may contain ingredients that are usually added in the manufacture of foods, as well as the extract as an active ingredient. Examples of the added ingredients include proteins, carbohydrates, fats, nutrients, seasonings, and flavoring agents. Examples of the carbohydrates include: typical saccharides, such as monosaccharides (e.g., glucose and fructose), disaccharides (e.g., maltose, sucrose, and oligosaccharides), and polysaccharides (e.g., dextrin and cyclodextrin); and sugar alcohols, such as xylitol, sorbitol, and erythritol. Examples of the flavoring agents may include natural flavoring agents (thaumatin, and *stevia* extracts (e.g., rebaudioside A, glycyrrhizin, etc.)) and synthetic flavoring agents (saccharin, aspartame, etc.). For example, the food composition of the present disclosure, when prepared as a drink, may contain citric acid, liquefied fructose, sugar, glucose, acetic acid, malic acid, fruit juice, an *Eucommia ulmoides* extract, a jujube extract, a licorice extract, and the like, in addition to the extract of the present disclosure.

Since, like "the pharmaceutical composition for treatment of attention deficit hyperactivity disorder", the food composition for alleviation of attention deficit hyperactivity disorder contains, as an active ingredient, the same mixture extract of Longan Arillus, Salviae Miltiorrhizae Radix, Gastrodiae Rhizoma, and Liriopis seu Ophiopogonis Tuber, a description of overlapping contents therebetween is omitted to avoid excessive redundancy of the present specification.

In accordance with still another aspect of the present invention, there is provided a method for alleviation or treatment of attention deficit hyperactivity disorder, the method including administering a composition to a subject suffering from attention deficit hyperactivity disorder, the composition containing, as an active ingredient, a mixture extract of Longan Arillus, Salviae Miltiorrhizae Radix, Gastrodiae Rhizoma, and Liriopis seu Ophiopogonis Tuber.

In an embodiment of the present disclosure, the composition is a pharmaceutical composition or a food composition.

In a specific embodiment of the present disclosure, the mixture extract of Longan Arillus, Salviae Miltiorrhizae Radix, Gastrodiae Rhizoma, and Liriopis seu Ophiopogonis Tuber is prepared by mixing respective extracts of Longan Arillus, Salviae Miltiorrhizae Radix, Gastrodiae Rhizoma, and Liriopis seu Ophiopogonis Tuber or by subjecting a mixture of Longan Arillus, Salviae Miltiorrhizae Radix, Gastrodiae Rhizoma, and Liriopis seu Ophiopogonis Tuber to extraction.

In another embodiment of the present disclosure, the extraction method, mixing ratio, concentration method, and drying method of the mixture extract are as described with respect to the preparation process of the mixture extract.

As used herein, the term "administration" or "administer" refers to a method of administering a therapeutically effective amount of the composition of the present disclosure to a subject (object) suffering from attention deficit hyperactivity disorder whereby the same amount thereof is formed in the body of the subject.

The term "therapeutically effective amount" of the composition refers to a content of the composition, which is sufficient to provide a therapeutic or prophylactic effect to a subject, to which the composition is to be administered, and thus the term has a meaning encompassing "prophylactically effective amount". As used herein, the term "subject" is a mammal including a human, a mouse, a rat, a guinea pig, a dog, a cat, a horse, a cow, a pig, a monkey, a chimpanzee, a baboon, a rhesus monkey, and the like. Most specifically, the subject of the present disclosure is a human.

Since the method for alleviation or treatment of attention deficit hyperactivity disorder of the present disclosure includes a step of administering the composition according to an aspect of the present disclosure, which contains as an active ingredient a mixture extract of Longan Arillus, Salviae Miltiorrhizae Radix, Gastrodiae Rhizoma, and Liriopis seu Ophiopogonis Tuber, a description of overlapping contents therebetween is omitted to avoid excessive redundancy of the present specification.

Features and advantages of the present disclosure are summarized as follows.

(a) The present disclosure relates to a pharmaceutical composition for treatment of attention deficit hyperactivity disorder and a food composition for alleviation of attention deficit hyperactivity disorder, each of which contains as an active ingredient a mixture extract of Longan Arillus, Salviae Miltiorrhizae Radix, Gastrodiae Rhizoma, and Liriopis seu Ophiopogonis Tuber.

(b) The composition containing as an active ingredient a mixture extract of Longan Arillus, Salviae Miltiorrhizae Radix, Gastrodiae Rhizoma, and Liriopis seu Ophiopogonis Tuber of the present disclosure inhibits the hyperactivity of glutamate receptors, which is known to be a cause of attention deficit hyperactivity disorder, alleviates clinical symptoms (attention decrease and hyperactivity) of child patients, and shows an improvement effect in fMRI examination results, and thus can be advantageously used as a medicine for attention deficit hyperactivity disorder or a food for alleviation of attention deficit hyperactivity disorder.

BRIEF DESCRIPTION OF THE DRAWINGS

The above and other aspects, features and advantages of the present disclosure will be more apparent from the following detailed description taken in conjunction with the accompanying drawings.

DETAILED DESCRIPTION

Figure 1:
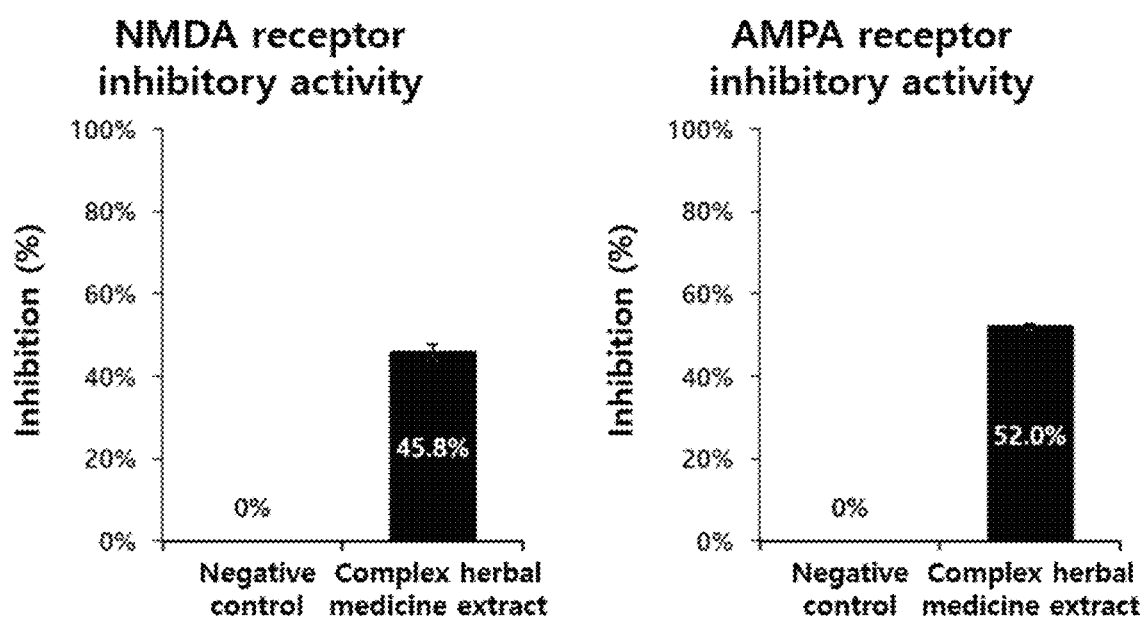
FIG. 1 shows inhibitory effects of the mixture extract of Longan Arillus, Salviae Miltiorrhizae Radix, Gastrodiae Rhizoma, and Liriopis seu Ophiopogonis Tuber of the present disclosure on glutamate receptor (NMDA or AMPA receptor)-ligand binding.

Hereinafter, the present disclosure will be described in more detail with reference to exemplary embodiments. These exemplary embodiments are provided only for the purpose of illustrating the present disclosure in more detail, and therefore, according to the purpose of the present disclosure, it would be apparent to a person skilled in the art that these examples are not construed to limit the scope of the present disclosure.

EXAMPLES

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

Preparative Example 1: Preparation of Inventive Complex Herbal Medicine Extract of Longan Arillus, Salviae Miltiorrhizae Radix, Gastrodiae Rhizoma, and Liriopis Seu Ophiopogonis Tuber Longan Arillus, Salviae Miltiorrhizae Radix, Gastrodiae Rhizoma, and Liriopis seu Ophiopogonis Tuber, which have been washed and dried, were purchased and used in the following tests (Humanherb, Korea). The herb medicines Longan Arillus, Salviae Miltiorrhizae Radix, Gastrodiae Rhizoma, and Liriopis seu Ophiopogonis Tuber were mixed at a weight ratio of 3:3:1:5, and then water is added thereto with a volume corresponding to 10 times the total weight of the mixture, followed by extraction under reflux at 90±5° C. for 3 hours. The extract was filtered, concentrated under reduced pressure at 60° C., and freeze-dried, to thereby give an inventive complex herbal medicine extract powder at a yield of 46.48%.

Test Example 1: Inhibitory Effect of Complex Herbal Medicine Extract on Glutamate Receptor-Ligand Binding To investigate the treatment effects of the inventive complex herbal medicine extract produced by the method in Preparative Example 1 on attention deficit hyperactivity disorder (ADHD), the effects of the complex herbal medicine extract on the activation of glutamate receptors, which is known to be associated with a cause of ADHD was investigated.

Specifically, the effects on glutamate receptor-ligand binding was determined through radio-ligand binding assay. Membranes containing glutamate receptors (NMDA receptor and AMPA receptor) used in the tests were isolated from the cerebral cortex of 6-week-old male Wistar rats weighing 175±25 g (BioLASCO, Taiwan). i) For NMDA receptor-ligand binding, 2.5 mg of membranes were allowed to react with 2 nM [$^3$H]CGP-39653 (PerkinElmer, USA), which is a radioisotope-labeled ligand, and 30 μg/ml of the complex herbal medicine extract in a buffer (50 mM Tris-HCl, pH 7.4) at 4° C. for 20 minutes. Thereafter, the membranes were filtered and washed, and the amount of radioisotopes remaining on the filter was measured as the counter per minute (cpm) by using a scintillation counter, thereby quantifying the amount of ligand specifically binding to the NMDA receptor. ii) For AMPA receptor-ligand binding, 5 mg of membranes were allowed to react with 5 nM [$^3$H]AMPA (PerkinElmer, USA), which is a radioisotope-labeled ligand, and 30 μg/ml of the complex herbal medicine extract in a buffer (50 mM Tris-HCl, pH 7.4, 200 mM KSCN) at 37° C. for 20 minutes. Thereafter, the membranes were filtered and washed, and the amount of radioisotopes remaining on the filter was measured as the counter per minute (cpm) by using a scintillation counter, thereby quantifying the amount of ligand specifically binding to the AMPA receptor. For each of the tests, a non-treatment group was used as a negative control, and 1 mM L-glutamic acid (Sigma-Aldrich, USA) was used for non-specific binding. A reduction in radiation dose at the time of treatment with the complex herbal medicine extract was expressed as receptor inhibitory activity (%) by using the following calculation formula.

[Calculation Formula]

Receptor inhibitory activity (%)=[1−((mean count per minute (cpm) of sample)−(mean count per minute (cpm) of non-specific binding substance))/((mean count per minute (cpm) of negative control)−(mean count per minute (cpm) of non-specific binding substance))]×100

TABLE 1

| Type of receptor | Test group | Treatment substance | | First round of test | Second round of test | Mean | Mean inhibitory activity (%) |
|---|---|---|---|---|---|---|---|
| NMDA receptor | Negative control | 2 nM [$^3$H]CGP-39653 | +Non-treatment | 1431 | 1420 | 1431 ± 11 | 0 |
| | Composite herbal medicine extract | | +30 μg/mL extract | 836 | 780 | 808 ± 28 | 45.8 ± 2.0 |
| | Non-specific binding substance | | +1 mM L-glutamic acid | 80 | 59 | 70 ± 11 | — |
| AMPA receptor | Negative control | 5 nM [$^3$H]AMPA | +Non-treatment | 3799 | 3861 | 3830 ± 8 | 0 |
| | Composite herbal medicine extract | | +30 μg/mL extract | 1875 | 1917 | 1896 ± 28 | 52.0 ± 0.6 |
| | Non-specific binding substance | | +1 mM L-glutamic acid | 98 | 122 | 110 ± 15 | — |

As shown in Table 1 and FIG. 1, the inhibitory effects of the inventive complex herbal medicine extract on the NMDA receptor and the AMPA receptor, which are glutamate receptors, were 46% and 52%, respectively. The results indicate that the complex herbal medicine extract can exhibit antagonistic efficacy by inhibiting the binding of glutamate to the respective receptors. It can be therefore seen that the inventive complex herbal medicine extract effectively inhibits the binding between glutamate receptors and ligands, and thus exhibit efficacy on attention deficit hyperactivity disorder.

Test Example 2: Effects of Complex Herbal Medicine Extract on ADHD Patients

The actual effects of the inventive complex herbal medicine extract exhibiting inhibitory effects on the NMDA and AMPA receptors as shown in Test Example 1 on ADHD patients were investigated. Tests were conducted on elementary, middle, and high school students receiving methylphenidate among ADHD child patients who are being treated at the Department of Psychiatry at Chung-Ang University Hospital, and detailed criteria for selection of the subjects were as follows.

Criteria for Selection
(1) Child and adolescent patients aged 6-18 years;
(2) Patients diagnosed with ADHD according to the DSM-IV diagnostic criteria;
(3) Patients receiving methylphenidate as a medicine
(4) IQ of 80 or higher;
(5) Patients not having received methylphenidate drug treatment in the past; and
(6) Patients and their guardians who voluntarily consented to participate in the study after sufficient explanation of what study participants should know from a study director or a person delegated to be responsible for the study director.

Fourteen subjects satisfying the above selection criteria were divided into a placebo-administered group and an administration group of the inventive complex herbal medicine extract (600 mg/day) in a blind state, and the subjects took each test substance and methylphenidate together for 4 weeks. K-ARS, which is a clinical scale, and brain rs-fMRI images before and after taking were measured and comparison analyzed. The details of each test method were as follows.

2-1. Assessment of K-ARS (ADHD Rating Scale)

K-ARS is a behavior assessment questionnaire on the basis of diagnostic criteria presented in the diagnostic and statistical manual of mental disorder (DSM), and is used to assess the degree of ADHD symptoms of subjects from the responses of parents and guardians of ADHD child patients.

Figure 2:
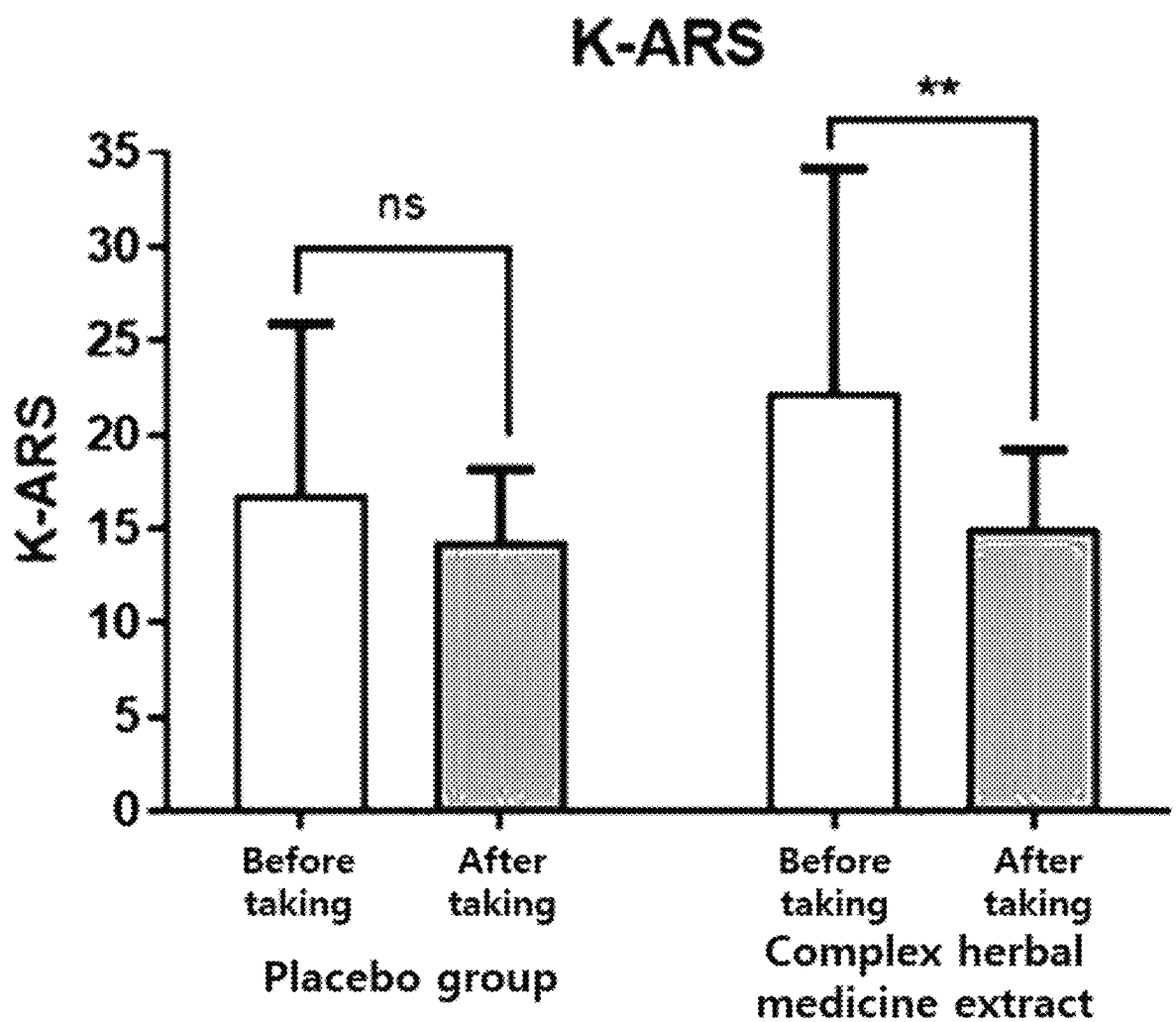
FIG. 2 shows clinical scale changes in inattentiveness and hyperactivity impulsivity of ADHD child patients before and after ADHD child patients took the mixture extract of Longan Arillus, Salviae Miltiorrhizae Radix, Gastrodiae Rhizoma, and Liriopis seu Ophiopogonis Tuber of the present disclosure.

*The K-ARS results before and after taking of the inventive complex herbal medicine extract are shown in Table 2 and FIG. 2.

TABLE 2

| K-ARS | Before taking | After taking |
| --- | --- | --- |
| Placebo group | 16.88 ± 9.03 | 14.38 ± 10.68$^{ns}$ |
| Complex herbal medicine extract | 22.20 ± 11.95 | 15.00 ± 9.41 ** |

As shown in Table 2 and FIG. 2, the K-ARS clinical scale of the ADHD child patients decreased by 32.43% from 22.30 to 15.00 (p=0.0100) when the child patients took the inventive complex herbal medicine extract for 4 weeks. It can be seen from the above results that the inventive complex herbal medicine extract showed efficacy to reduce inattentiveness and hyperactivity impulsivity of the ADHD child patients.

2.2 Resting-State Functional Magnetic Resonance Imaging (rs-fMRI) Assessment fMRI is a technique that images changes in cerebral blood flow, whereby blood oxygen level dependent (BOLD) images are acquired to observe the activity of each brain region. fMRI is a non-invasive, non-radioactive, and radioactivity-irrelevant test. Through this technique, the resting-state fRMI (rs-fMRI) of the brains of the subjects was analyzed, that is, the brains of participants in a state of not doing anything, were photographed, and image analyzed.

There have been many reports that ADHD patients showed a reduction in activity in various regions of the brain compared with normal persons and, especially, a deterioration in inhibition/control of the frontal lobe compared with ordinary persons (Liu et al., Oncotarget 8(27):44785-44799, 2017). Therefore, the left transverse temporal gyrus (BA 42) and the left cingulate gyrus (BA 31), which are brain regions associated with concentration, were subjected to activity comparison. The results are shown in Tables 3 and 4 and FIGS. 3A and 3B and 4.

TABLE 3

Changes in activity of left transverse temporal gyrus and left cingulate gyrus before and after taking of inventive complex herbal medicine extract

| Classification | Before taking | After taking | Change |
| --- | --- | --- | --- |
| left transverse temporal gyrus (BA42) | | | |
| Placebo group | 0.55 ± 0.11 | 0.18 ± 0.11 | −0.36 ± 0.15 |
| Complex herbal medicine extract | −0.15 ± 0.16 | 0.85 ± 0.13 | 0.99 ± 0.25 |
| left cingulate gyrus (BA31) | | | |
| Placebo group | 0.36 ± 0.12 | −0.03 ± 0.13 | −0.40 ± 0.22 |
| Complex herbal medicine extract | −0.42 ± 0.11 | 0.42 ± 0.13 | 0.84 ± 0.21 |

Figure 3A:
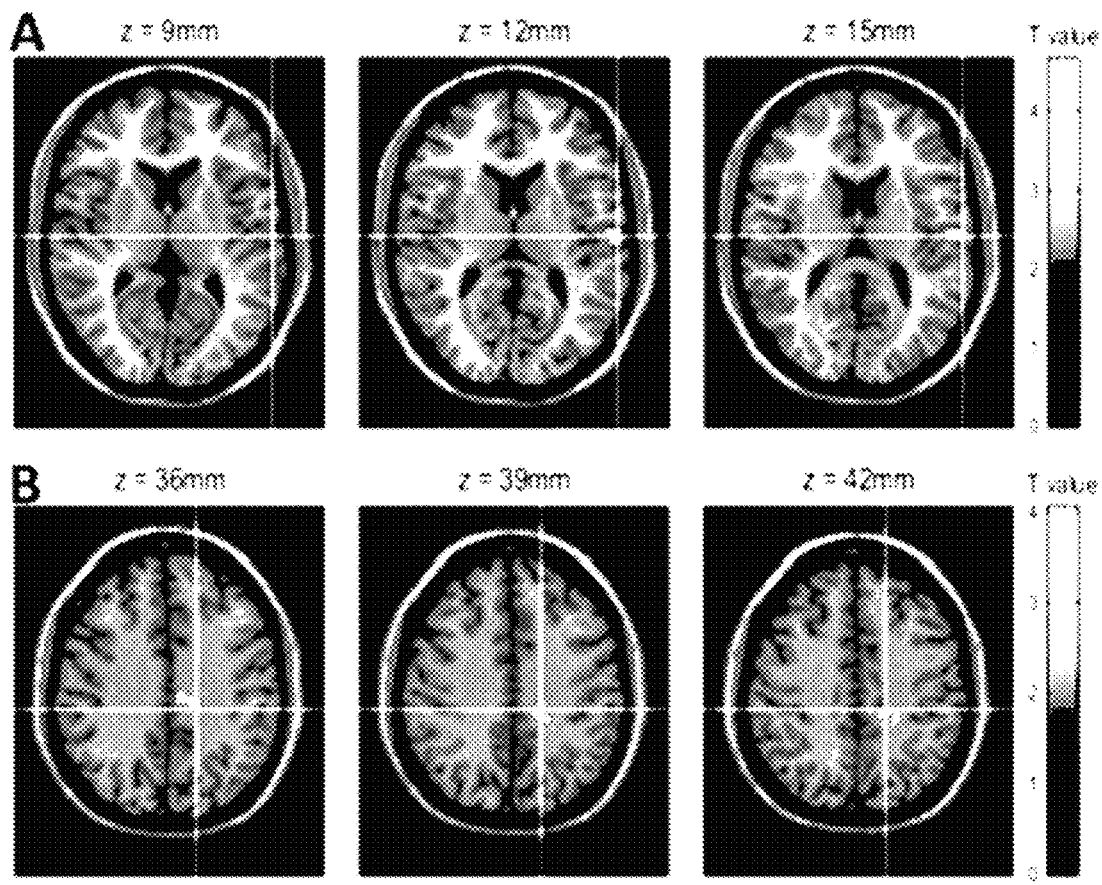
FIGS. 3A and 3B show the activities of the left transverse temporal gyrus and left cingulate gyrus, which are the brain regions associated with concentration of ADHD patients, before and after ADHD child patients took the mixture extract of Longan Arillus, Salviae Miltiorrhizae Radix, Gastrodiae Rhizoma, and Liriopis seu Ophiopogonis Tuber of the present disclosure.
Figure 3B:
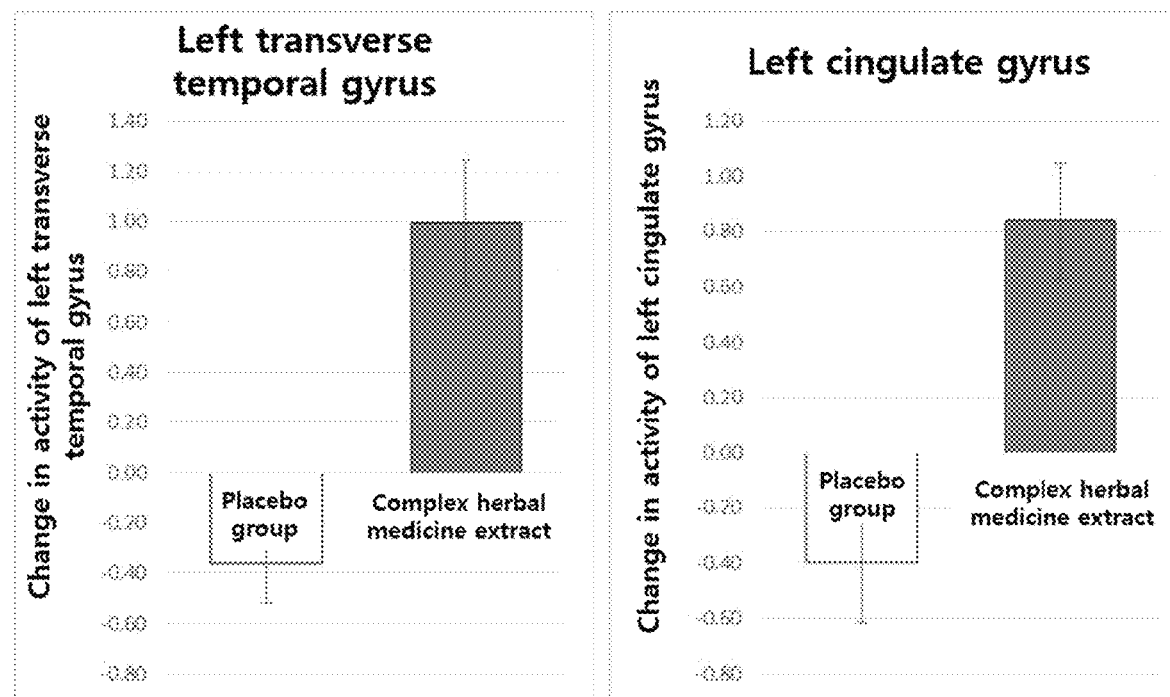

As shown in Table 3 and FIGS. 3A and 3B, the activity of the left transverse temporal gyrus and the activity of the left cingulate gyrus increased by 0.99 and 0.84, respectively, when the inventive complex herbal medicine extract was taken for 4 weeks. It can be seen from the results that the inventive complex herbal medicine extract induced the activation of the brain regions associated with attention of the ADHD child patients.

In addition, ADHD patients showed a deterioration in connectivity of the brain compared with normal persons, and studies on the correlation between connectivity of the cerebral white matter and attention are currently being actively conducted (Nagel et al., J Am Acad Child Adolesc Psychiatry 50(3):283-292, 2011). Therefore, the effect of the complex herbal medicine extract on the functional connectivity changes of the left cingulate cortex and the left middle occipital gyrus with the posterior cingulate cortex were investigated. The results are shown in Table 4 and FIGS. 4A and 4B.

TABLE 4

Changes in functional connectivity of left cingulate cortex and left middle occipital gyrus with posterior cingulate cortex before and after taking complex herbal medicine

| Classification | Before taking | After taking | Change |
|---|---|---|---|
| left cingulate cortex | | | |
| Placebo group | 0.0619 ± 0.0235 | −0.1373 ± 0.0317 | −0.1991 ± 0.0417 |
| Complex herbal medicine extract | −0.1442 ± 0.0428 | 0.0568 ± 0.0258 | 0.2010 ± 0.0472 |
| left middle occipital gyrus | | | |
| Placebo group | 0.3096 ± 0.0574 | 0.0538 ± 0.0334 | −0.2558 ± 0.0728 |
| Complex herbal medicine extract | −0.0029 ± 0.0532 | 0.1835 ± 0.0469 | 0.1864 ± 0.0788 |

Figure 4A:
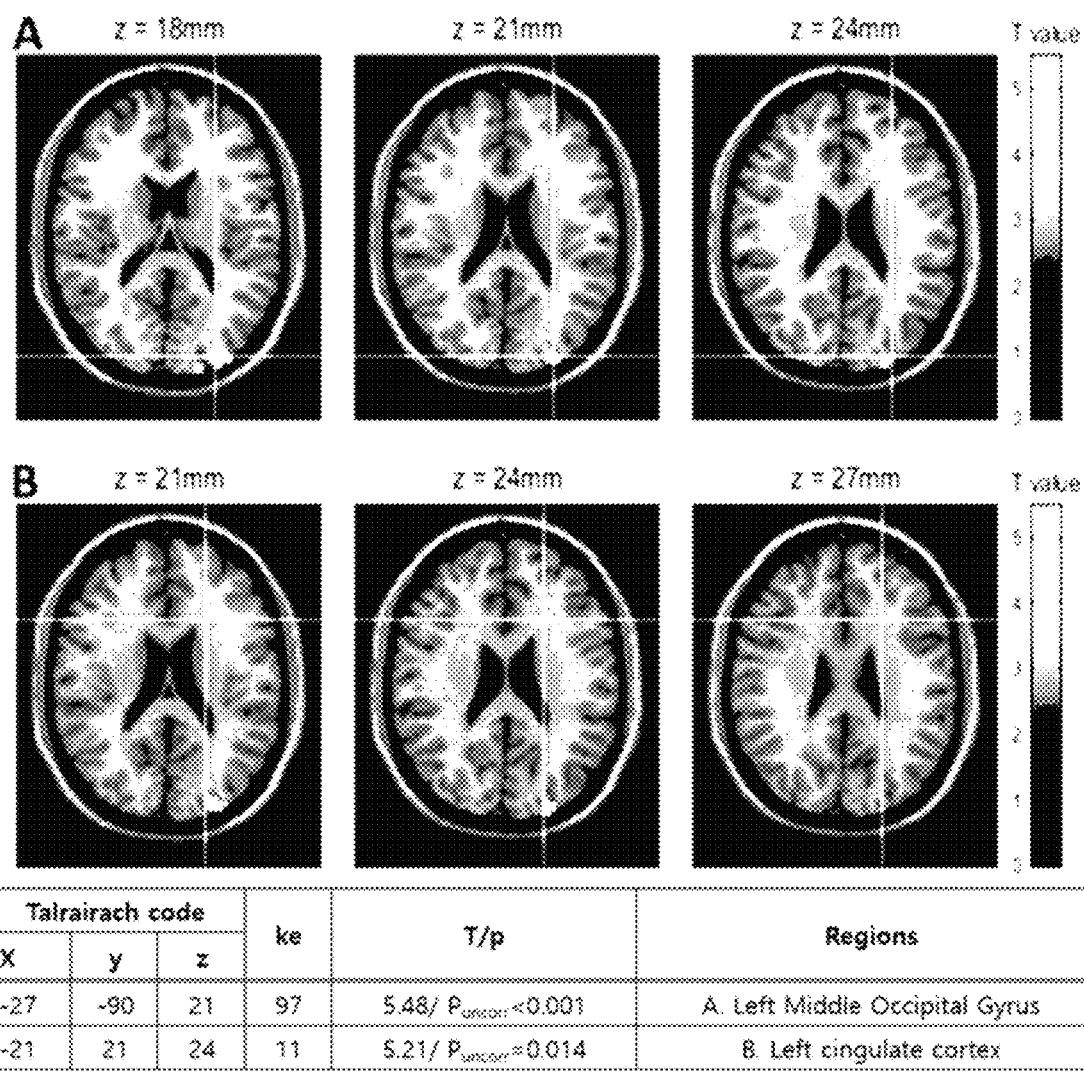
FIGS. 4A and 4B show the changes in functional connectivity of the left cingulate cortex and the left middle occipital gyrus with the posterior cingulate cortex in the brain of ADHD patients before and after ADHD child patients took the mixture extract of Longan Arillus, Salviae Miltiorrhizae Radix, Gastrodiae Rhizoma, and Liriopis seu Ophiopogonis Tuber of the present disclosure.
Figure 4B:
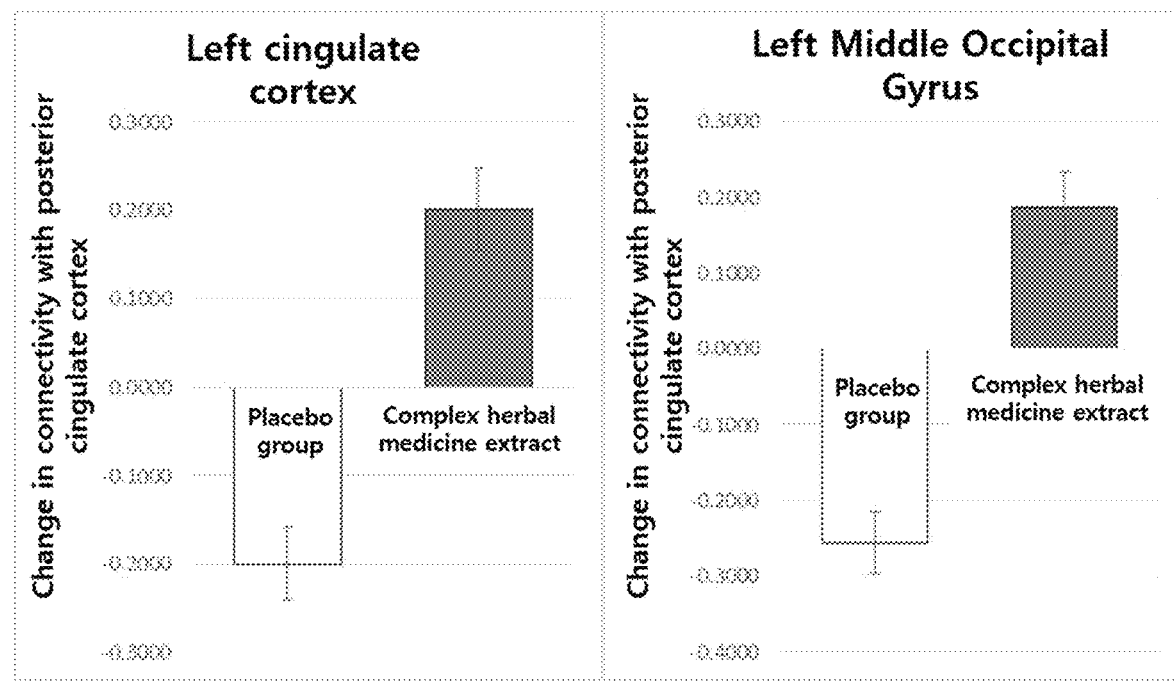

As shown in Table 4 and FIGS. 4A and 4B, the connectivity increased by 0.2010 for the left cingulate cortex and 0.1864 for the left middle occipital gyrus when the complex herbal medicine extract was taken for 4 weeks. It can be seen from the results that the inventive complex herbal medicine extract showed effects of increasing functional connectivity of the brain in ADHD child patients.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A pharmaceutical composition for treatment of attention deficit hyperactivity disorder (ADHD), the pharmaceutical composition comprising:
    (a) as an active ingredient, a mixture extract of Longan Arillus, Salviae Miltiorrhizae Radix, Gastrodiae Rhizoma, and Liriopis seu Ophiopogonis Tuber; and
    (b) a pharmaceutically acceptable carrier.
2. The pharmaceutical composition of claim 1, wherein the extract is obtained by extraction with an organic solvent, water, or a mixed solvent thereof.
3. The pharmaceutical composition of claim 2, wherein the organic solvent is selected from the group consisting of C1 to C6 lower alcohols, petroleum ether, hexane, benzene, chloroform, methylene chloride, ethers, ethyl acetate, and acetone.
4. The pharmaceutical composition of claim 1, wherein the Liriopis seu Ophiopogonis Tuber is obtained from Liriope *platyphylla* or Ophiopogon japonicas.
5. The pharmaceutical composition of claim 1, wherein the mixing weight ratio of Longan Arillus, Salviae Miltiorrhizae Radix, Gastrodiae Rhizoma, and Liriopis seu Ophiopogonis Tuber is 1-10:1-10:1-10:1-10.
6. The pharmaceutical composition of claim 1, further comprising methylphenidate.
7. A food composition for alleviation of attention deficit hyperactivity disorder, the food composition comprising, as an active ingredient, a mixture extract of Longan Arillus, Salviae Miltiorrhizae Radix, Gastrodiae Rhizoma, and Liriopis seu Ophiopogonis Tuber.
8. A method for alleviation or treatment of attention deficit hyperactivity disorder, the method comprising administering a composition to a subject suffering from attention deficit hyperactivity disorder, the composition comprising, as an active ingredient, a mixture extract of Longan Arillus, Salviae Miltiorrhizae Radix, Gastrodiae Rhizoma, and Liriopis seu Ophiopogonis Tuber.
9. The method of claim 8, further comprising administering methylphenidate to the subject.

* * * * *